United States Patent
Xia

(10) Patent No.: US 10,953,025 B2
(45) Date of Patent: Mar. 23, 2021

(54) COMPOSITION, DEVICE AND METHOD FOR DELAYED AND SUSTAINED RELEASE OF BRAIN ENERGY MOLECULES

(71) Applicant: ABLE CEREBRAL, LLC, Ephrata, PA (US)

(72) Inventor: Jun Xia, York, PA (US)

(73) Assignee: Able Cerebral, LLC, Ephrata, PA (US)

( * ) Notice: Subject to any disclaimer, the term of this patent is extended or adjusted under 35 U.S.C. 154(b) by 0 days.

(21) Appl. No.: 15/983,085

(22) Filed: May 17, 2018

(65) Prior Publication Data

US 2018/0264019 A1 Sep. 20, 2018

Related U.S. Application Data

(63) Continuation-in-part of application No. 14/232,613, filed as application No. PCT/US2012/046782 on Jul. 13, 2012, now Pat. No. 10,016,370, application No. 15/983,085, which is a continuation-in-part of application No. PCT/US2016/062794, filed on Nov. 18, 2016, and a continuation-in-part of application No. 15/521,274, filed as application No. PCT/US2015/056537 on Oct. 20, 2015, now abandoned.

(60) Provisional application No. 61/572,258, filed on Jul. 14, 2011, provisional application No. 62/386,152, filed on Nov. 19, 2015, provisional application No. 62/123,328, filed on Nov. 14, 2014, provisional application No. 62/122,457, filed on Oct. 21, 2014.

(51) Int. Cl.
| | |
|---|---|
| *A61K 9/20* | (2006.01) |
| *A61K 9/70* | (2006.01) |
| *A61M 21/00* | (2006.01) |
| *A61K 31/7004* | (2006.01) |
| *A61K 9/00* | (2006.01) |
| *A61K 9/28* | (2006.01) |
| *A61K 47/22* | (2006.01) |
| *A61K 47/12* | (2006.01) |
| *A61K 31/437* | (2006.01) |
| *A61M 21/02* | (2006.01) |
| *A61K 47/10* | (2017.01) |
| *A61K 47/20* | (2006.01) |

(52) U.S. Cl.
CPC ........ *A61K 31/7004* (2013.01); *A61K 9/0014* (2013.01); *A61K 9/0053* (2013.01); *A61K 9/2013* (2013.01); *A61K 9/2846* (2013.01); *A61K 9/2866* (2013.01); *A61K 9/2886* (2013.01); *A61K 9/7023* (2013.01); *A61K 31/437* (2013.01); *A61K 47/10* (2013.01); *A61K 47/12* (2013.01); *A61K 47/20* (2013.01); *A61K 47/22* (2013.01); *A61M 21/02* (2013.01); *A61K 9/2018* (2013.01); *A61K 9/2054* (2013.01); *A61M 2021/0077* (2013.01); *A61M 2230/10* (2013.01); *A61M 2230/18* (2013.01)

(58) Field of Classification Search
None
See application file for complete search history.

(56) References Cited

U.S. PATENT DOCUMENTS

| | | | |
|---|---|---|---|
| 6,770,635 B1 * | 8/2004 | Drube ................ | A61K 31/7012 514/62 |
| 2002/0098242 A1 * | 7/2002 | Darder ................ | A61K 9/5078 424/490 |
| 2005/0186278 A1 * | 8/2005 | Pierro Francesco ... | A61K 9/282 424/472 |
| 2007/0148195 A1 * | 6/2007 | Ebert ................... | A61K 31/216 424/400 |

FOREIGN PATENT DOCUMENTS

| | | | |
|---|---|---|---|
| WO | WO9743989 | * | 11/1997 |
| WO | WO2013010137 | * | 1/2013 |
| WO | WO2016064932 | * | 4/2016 |

OTHER PUBLICATIONS

Levina et al., The influence of excipients on drug release from hydroxypropyl methylcellulose matrices, Journal of Pharmaceutical Sciences, vol. 93, No. 11, Nov. 2004 (Year: 2004).*

* cited by examiner

*Primary Examiner* — Jennifer A Berrios
(74) *Attorney, Agent, or Firm* — Rodney J. Fuller; Booth Udall Fuller, PLC

(57) ABSTRACT

The present invention relates to compositions, devices and methods of delayed and sustained release of energy molecules for brain function. The composition comprises an energy molecule required for human brain function; wherein the release of the energy molecule is delayed and then sustained over a period of time. The methods comprise administering the composition subject in need thereof immediately prior to going to sleep. The present invention also relates to systems for brain stimulation during sleep and methods of use thereof. The system comprises a brain stimulation module and at least one of a brain energy source, a hypnotic source, or both. The methods involve administering to a subject a brain energy molecule, a hypnotic, or both and providing to the subject during restorative sleep a sensory stimulation.

19 Claims, No Drawings

COMPOSITION, DEVICE AND METHOD FOR DELAYED AND SUSTAINED RELEASE OF BRAIN ENERGY MOLECULES

CROSS REFERENCE TO RELATED APPLICATIONS

This application is a continuation-in-part application of U.S. patent application Ser. No. 14/232,613, filed on Jan. 13, 2014 (published as US20140180224), which is the U.S. National Stage of International Application No. PCT/US2012/046782, filed on Jul. 13, 2012, which claims the benefit of U.S. Provisional Patent Application No. 61/572,258, filed on Jul. 14, 2011; this application is also a continuation-in-part application of International Application No. PCT/US2016/062794, filed on Nov. 18, 2016, which claims the benefit of U.S. Provisional Application No. 62/386,152, filed on Nov. 19, 2015; and a continuation-in-part application of U.S. patent application Ser. No. 15/521,274, filed on Apr. 21, 2017 (published as US 20170304582), which is the U.S. National Stage of International Application No. PCT/US2015/056537, filed on Oct. 20, 2015, which claims the benefit of U.S. Provisional Patent Application No. 62/122,457, filed on Oct. 21, 2014 and U.S. Provisional Patent Application No. 62/123,328, filed on Nov. 14, 2014; the contents of each of which are hereby incorporated herein by reference in their entireties.

FIELD OF THE INVENTION

This invention relates to the delayed and controlled release of energy molecules useful for brain function. More particularly the invention relates to delayed and sustained release of glucose, mannose, lactic acid (lactate) and pyruvic acid (pyruvate) for brain energy supply via oral and transdermal formulations. The invention also relates to systems and methods of brain stimulation during sleep, including directing the subject matter, increasing the vividness of a dream, or both.

BACKGROUND OF THE INVENTION

Hypoglycemia, especially, nocturnal hypoglycemia, is not a well-managed disease. Even though hypoglycemic episodes may lead to impaired epinephrine response and diminished neurological function, patients ignore the disease due to the lack of a practical solution on the market and ignorance of the long-term impact on their health. Symptoms of nocturnal hypoglycemia are usually subtle and may include nightmares, morning fatigue, and headache. More serious symptoms, although rare, sometimes appear and include seizures and loss of consciousness.

Unrecognized hypoglycemic episodes are known to occur in 62.5% of type-1 diabetic patients and in 46.6% of type-2 diabetic patients, with the majority (73.7%) of all events occurring at night. It has been shown that a very high incidence of nocturnal asymptomatic hypoglycemic episodes occur in type-2 diabetic subjects treated with oral agents. Research has shown that most nocturnal hypoglycemic episodes happen around 3 am, and last longer than hypoglycemic episodes that occur at other times, with a medium duration of 3 hours.

Typically treatments for hypoglycemia are designed for immediate, preferably instantaneous, increase in blood sugar level. For example, a commercial chewable tablet for day time hypoglycemia rescue contains 4000 mg, and the instructions for use is to take at least one to two tablets within very short period of time—minutes. For prevention of too low blood sugar, prominent products on the market, such as GLUCERNA™ shakes or bars, claim to maintain glucose level for a maximum of 3 to 4 hours, which is too short for the typical period of evening rest. Other efforts, such as U.S. Patent Application US2012/0015039, apply controlled-release technology for carbohydrates and other nutrients for sustainable delivery for only about 3 hours in order to enhance athletic performance, increase eye-hand coordination and maintain concentration on the task at hand. Similar efforts can be found in U.S. Pat. Nos. 7,943,163; 6,534,487; 5,576,306; 6,905,702; 6,316,427; 5,776,887; EP06747611; and WO2009/051786 which are hereby incorporated by reference.

U.S. Pat. No. 6,815,436 describes making granules of cornstarch for controlled enzymatic breakdown of amylose and amylopectin. Similarly, U.S. Pat. No. 6,316,427 describes using an uncooked cornstarch product for bedtime ingestion to slowly release carbohydrates. U.S. Pat. No. 5,776,887 describes a diabetic nutritional product for controlled absorption of carbohydrates by delivering "a rapidly absorbed fraction such as glucose or sucrose, a moderately absorbed fraction such as certain cooked starches or fructose, and a slowly absorbed fraction such as raw corn starch."

Controlled release of carbohydrates with initial release of sugars and lasting about 3-4 hours has been demonstrated. These efforts, however, come with unnecessary nutrients such as vitamins, minerals (such as sodium), and lipids which might have ill-effects for a sleeping individual. Additionally, the previous efforts have suggested delivering long-chain carbohydrates, which not only deliver an unpleasant fullness in the stomach, but also trigger digestion during sleep, and may disturb enzyme secretion thereby causing obesity in type-1 and -2 diabetes patients. A need exist for a composition that is effective at treating and managing hypoglycemia and especially without the side effects.

BRIEF SUMMARY OF THE INVENTION

The present invention is directed to a composition, method, and device for delayed and sustained release of energy molecules. One embodiment of the invention provides compositions to accurately manage nocturnal hypoglycemia. The composition preferably comprises one or more of the following brain energy molecules: glucose, mannose, lactic acid (lactate), and pyruvic acid (pyruvate). The four energy molecules most preferably delivered with this invention are utilized by the brain, especially of a human, for energy support. These four energy molecules do not require the human body to further digest during sleep. Thus, one embodiment of the composition prevents diabetes patients from further weight gain. The composition of the invention may include the energy molecules individually, or in combination of two, three, or four. In some aspects, the composition may be in any one of the following solid forms: a capsule, a cachet, a pill, a tablet, a powder, a granule, a pellet, a bead, a particle, or a transdermal patch.

One embodiment of the invention includes delayed and sustained release of energy molecules which may provide patients taking tablets or capsules at bedtime to not be disturbed for their normal initial sleeping pattern. By delayed and sustained release of energy molecules for up to 8 hours, early morning hypoglycemia may be eliminated. The transdermal delivery device presented in this invention may provide the advantage of therapeutic management for early morning hypoglycemia. By applying the transdermal device near neck areas, the energy molecules typically directly penetrate into carotid arteries and are further transported to the central nervous system (CNS). Preferably, the transdermal delivery device of this invention also provides a near zero-order delivery of the energy molecules for a sustained period of at least 6-10 hours. One embodiment of the current invention allows patients to easily stop the energy molecule delivery by simply peeling off the device from their skin when they wake up in the morning.

One embodiment of the current invention provides a delayed and sustained release composition comprising an energy molecule required for human brain function; wherein less than 15% by weight of the energy molecule is released within 2 hours after administration, the energy molecule being released at a sustained rate after 2 hours, wherein less than 60% of the energy molecule is released within the first 4 hours of administration, and at least 80% of the energy molecule is released within 8 hours after administration.

A further embodiment provides wherein the energy molecule is selected from the group consisting of: glucose, mannose, lactic acid (lactate), and pyruvic acid (pyruvate). Lactic acid may be substituted for lactate, and pyruvic acid may be substituted for pyruvate.

A further embodiment provides a delayed and sustained release composition wherein the composition comprises a transdermal preparation, the preparation further comprising a skin permeation enhancer formulation comprising: at least one glycol selected from the group consisting of: propylene glycol, butylenes glycol, hexylene glycol, ethoxydiglycol, dipropylene glycol, and pentylene glycol; monothiogylcerol; at least one of 2-methyl-3-hydroxypyranone or 2-ethyl-3-hydroxypyranone; and an aliphatic carboxylic acid of 8 to 24 carbon atoms or an ester of an aliphatic carboxylic acid of 8 to 24 carbon atoms with an aliphatic alcohol of 1 to 14 carbon atoms and 1 to 2 hydroxy groups.

A further embodiment provides a delayed and sustained release composition wherein the composition is in an oral tablet or capsule form.

A further embodiment provides a delayed and sustained release composition wherein the amount of the energy molecule is at least 50 or 100 milligrams (mg), for example, between about 150-2500 mg, 250-2500 mg, about 300-2550 mg, about 350-2500 mg, about 400-2500 mg, about 500-2500 mg, about 750-2500 mg or about 250-2000 mg.

In some aspects, the delayed and sustained release composition comprises, by weight, at least 20%, at least 25%, at least 30%, at least 35%, at least 40%, at least 45%, at least 50%, at least 55%, at least 60%, at least 65%, at least 70%, or at least 75% the energy molecule. In preferred embodiments, the delayed and sustained release composition comprises no more than 85% or 89% by weight energy molecule. For example, the delayed and sustained release composition comprises between 45-89% by weight energy molecule, between 50-75% by weight energy molecule, between 45-75% by weight energy molecule, or about 50% by weight energy molecule.

A further embodiment provides a delayed and sustained release composition comprising a coating of a pH-dependent polymer on the oral tablet.

A further embodiment provides a delayed and sustained release composition comprising a hydrophilic polymer.

A further embodiment provides a delayed and sustained release composition wherein the tablet further comprises a coating of a water-insoluble polymer.

A preferred embodiment provides a delayed and sustained release composition wherein less than 15% by weight of the energy molecule is released within 2 hours after administration in a simulated gastric fluid dissolution media; the energy molecule being released at a sustained rate after 2 hours, wherein less than 60% by weight of the energy molecule is released within the first 4 hours and at least 85% by weight of the energy molecule is released within 8 hours after administration in a simulated intestinal fluid dissolution media using USP dissolution method II at 50 rpm.

A further embodiment provides a delayed and sustained release composition wherein the pH-dependent polymer is selected from the group consisting of: a polyacrylate material, a cellulose acetate phthalate, cellulose phthalate hydroxy propyl methyl ether, polyvinyl acetate phthalate, hydroxy propyl methyl cellulose acetate succinate, cellulose acetate trimellitate, and shellac.

A further embodiment provides a delayed and sustained release composition wherein the hydrophilic polymer is selected from the group consisting of: hydroxy propyl methylcellulose, hydroxypropyl ethylcellulose, hydroxypropyl cellulose, hydroxy ethylcellulose, methylcellulose, xantham gums, alginate salts, polyethylene oxide, carboxyvinyl polymer, and a salt of a carboxymethyl cellulose, the hydrophilic polymer having a viscosity within the range of from about 60 to about 7,000,000 centipoises in a 2% by weight water solution at 25 degrees Celsius, as measured by a Brookfield LV viscometer.

A further embodiment provides a delayed and sustained release composition wherein the water-insoluble polymer is selected from the group consisting of: ethyl cellulose, acetate cellulose, and polyacrylate copolymer.

A further embodiment of the present invention provides a method for treating nocturnal hypoglycemia comprising administering to a subject in need thereof, the composition of claim 1 immediately prior to going to sleep.

A further embodiment of the present invention provides a transdermal delivery device comprising: a reservoir layer comprising absorbent materials inert to chemicals, the reservoir layer containing a composition comprising an energy molecule required for human brain function and a skin permeation enhancer formulation; an adhesive layer attached to the reservoir layer and configured to secure the device to the skin and seal it so as to prevent leaking; a backing layer coated by the adhesive layer and impermeable by the energy molecules and the enhancer mixture; a release liner that is inert to chemicals and protects the adhesive layer and the reservoir layer before being peeled off for administration, and configured to release the composition contained in the reservoir layer such that less than 10% by weight of the energy molecule is delivered to blood circulation within 2 hours after administration, the energy molecule being delivered at a sustained rate after 2 hours for a period of time up to at least 8 hours.

A further embodiment of the transdermal delivery device provides wherein the backing layer is impermeable to the energy molecules and the energy molecule is one or more molecules selected from the group consisting of: glucose, mannose, lactic acid (lactate), and pyruvic acid (pyruvate).

A further embodiment of the present invention provides a method for treating a subject having nocturnal hypoglycemia comprising placing the transdermal device on the subject's neck area proximate to the subject's carotid artery immediately prior to going to sleep.

A further embodiment provides a method wherein the device is configured to load the composition of energy molecule and enhancer mixture into the reservoir layer after detaching the release liner and before applying the device to the skin.

A further embodiment provides a method wherein the energy molecule is one or more molecules selected from the group consisting of: glucose, mannose, lactic acid (lactate), and pyruvic acid (pyruvate).

The present invention is also directed to a system for brain stimulation during sleep. The system comprises a brain stimulation module comprising a sensory stimulation unit, a recording unit, wherein the recording unit detects and records the stages of sleep, and a program to interpret the brain electrical activity as detected by the recording unit and direct the activation of the sensory stimulation unit. The program interprets the information from the recording unit so when the recording unit detects the subject is in restorative sleep, the program instructs the sensory stimulation unit to deliver sensory stimulation to the subject. The sensory stimulation may be at least one of sound, scent, taste, tactile, and visual stimulation. In some embodiments, the recording unit detects brain waves and records electroencephalography. In other embodiments, recording unit detects brain waves and records electroencephalography. In some implementations, restorative sleep is Stage 3 sleep, Stage REM sleep or indicated by the recording unit detecting rapid eye movements, delta waves, or rapid low-voltage EEG similar to when a person is awake.

The system further comprises at least one of a brain energy supply source, a hypnotic source, or a cholinergic molecule. The brain energy supply source comprises a brain energy molecule. The hypnotic source comprises a hypnotic. In preferred embodiments, the brain energy supply source comprises the brain energy molecule in a delayed and sustained release formulation. The hypnotic source may comprise the hypnotic in a delayed and sustained release formulation, an immediate release formulation, or sustained release formulation. The delayed and sustained release formulation is a formulation configured to release less than 15% by weight of the brain energy molecule and/or the hypnotic within 2 hours after administration. Preferably, less than 60% of the brain energy molecule and/or the hypnotic is released within the first 4 hours after administration, at least 80% of the brain energy molecule and/or the hypnotic is released within 8 hours after administration, and the brain energy molecule and/or the hypnotic is released at a sustained rate 2 hours after administration. The hypnotic source may also comprise the hypnotic in an immediate release formulation. The system providing brain stimulation to a sleeping subject to enhance the vividness of dreams as well as direct the subject matter of the dreams. Thus, the invention is also directed to methods of increasing vividness of a subject's dreams.

DETAILED DESCRIPTION OF THE INVENTION

Embodiments and applications of the invention presented here are described below. Unless specifically noted, it is intended that the words and phrases in the specification and the claims be given their plain, ordinary, and accustomed meaning to those of ordinary skill in the applicable arts.

As used herein, the term "about" refers to an range of ±2% or ±2 units from the point of reference.

The singular forms "a," "an," and "the" include plural referents unless the context clearly dictates otherwise. Thus, for example, reference to "a step" includes reference to one or more of such steps.

A preferred embodiment of a delayed and sustained release composition comprises an energy molecule required for human brain function. Energy molecules required for human brain function include molecules which do not require further digestion or enzymatic break down by the human body and are utilized by the human brain for energy support. In one embodiment, the energy molecule is glucose. In another embodiment the energy molecule is typically mannose, lactic acid (lactate) or pyruvic acid (pyruvate). In yet another embodiment the composition comprises a combination of two of these energy molecules.

The delayed and sustained release composition is configured to release less than 15% (e.g., less than 10%, 5%, and 2%), by weight, of the energy molecule within 2 hours after administration. After 2 hours, the energy molecule is preferably released at a sustained rate such that less than 60% (e.g., less than 55%, 50%, 40%), by weight of the energy molecule is released within the first 4 hours of administration, and at least 80% (e.g., at least 85%, 90%, or 95%), by weight, of the energy molecule is released within 8 hours after administration. In a more preferred embodiment, less than 5%, by weight, of the energy molecule is released within 2 hours after administration, less than 55% of the energy molecule is released within the first 4 hours and at least 85%, by weight, of the energy molecule is released within 8 hours after administration.

In certain embodiments, the delayed and sustained release composition is in a solid form, for example, a capsule, a cachet, a pill, a tablet, a powder, a granule, a pellet, a bead, a particle, or a transdermal patch. In some aspects, the beads or particles are used as the solid portion in a suspension liquid dosage form.

The delayed and sustained release composition preferably comprises a transdermal preparation for certain transdermal embodiments. The transdermal preparation typically includes a skin permeation enhancer formulation. A preferred embodiment of skin permeation enhancer formulation comprises at least one glycol, monothioglycerol, at least one of 2-methyl-3-hydroxypyranone or 2-ethyl-3-hydroxypyranone and an aliphatic carboxylic acid of 8 to 24 carbon atoms or an ester of said acid with an aliphatic alcohol of 1 to 14 carbon atoms and 1 to 2 hydroxy groups. In a more preferred embodiment, the skin permeation enhancer formulation has a composition of 10% to 95%, by weight, of the at least one glycol, 1% to 10%, by weight, of monothioglycerol, 2% to 30%, by weight, of the at least one of 2-methyl-3-hydroxypyranone or 2-ethyl-3-hydroxypyranone and 2%-10%, by weight, of the aliphatic carboxylic acid of 8 to 24 carbon atoms or an ester of said acid with an aliphatic alcohol of 1 to 14 carbon atoms and 1 to 2 hydroxy groups. The at least one glycol is typically selected from the group consisting of propylene glycol, butylenes glycol, hexylene glycol, ethoxydiglycol, dipropylene glycol and pentylene glycol. In a preferred embodiment, the skin permeation enhancer formulation has a composition of about 70-80%, by weight, butylene glycol, about 3-9%, by weight, monothioglycerol, about 10%, by weight, 2-methyl 3-hydroxy pyranones and about 4-12%, by weight, oleic acid. In a most preferred embodiment, the skin permeation enhancer formulation has a composition of about 76%, by weight, butylene glycol, about 6%, by weight, monothioglycerol, about 10%, by weight, 2-methyl 3-hydroxy pyranones and about 8%, by weight, oleic acid.

In certain embodiments, the delayed and sustained release composition comprises, by weight, at least 20%, at least 25%, at least 30%, at least 35%, at least 40%, at least 45%, at least 50%, at least 55%, at least 60%, at least 65%, at least 70%, or at least 75% the energy molecule. In preferred embodiments, the delayed and sustained release composition comprises no more than 85% or 89% by weight energy molecule. For example, the delayed and sustained release composition comprises between 45-85% by weight energy molecule, between 50-75% by weight energy molecule, between 45-75% by weight energy molecule, or about 50% by weight energy molecule.

In some aspects, the delayed and sustained release composition comprises at least 50 mg. In certain embodiments, such as for an adult subject, the delayed and sustained release composition comprises, at least 100 mg of the energy molecule, for example, between 50-2500 mg, about 100-2500 mg, about 150-2500 mg, 200-2500 mg, about 250-2500 mg, about 250-1750 mg, about 250-1250 mg, about 500-2500 mg, about 500-1750 mg, about 500-1250 mg, about 750-2500 mg, and about 1000-2500 mg. In a preferred embodiment, the delayed and sustained release composition comprises about 50 mg, 250 mg, 500 mg or 750 mg of the energy molecule.

In some aspects, the delayed and sustained release composition is an oral tablet. In certain embodiments, the oral tablets contains between about 50-2500 mg, for example between about 150-2500 mg or about 250-1250 mg of an energy molecule. In a preferred embodiment, the oral tablet contains between about 500-1000 mg of an energy molecule. In a more preferred embodiment, the oral tablet contains about 750 mg of an energy molecule. Other amounts of the energy molecule may also be contained in the oral tablet. Preferably, the tablets are designed to suitable sizes or compositions based on the age or physical characteristics of the patient as well as the severity of the disease.

Other suitable oral dosage forms include capsules and caplets. Preferred oral capsules contain contains between about 50 mg-2500 mg, for example between about 150-2500 mg or about 250-1250 mg, of an energy molecule. In a more preferred embodiment, the oral capsule contains between about 500-1000 mg of an energy molecule. In a most preferred embodiment, the oral capsule contains about 500-750 mg of an energy molecule e.g., 50-2000 mg, 250-1000 mg, 350-1500 mg, or 450-2000 mg. Other amounts of the energy molecule may also be contained in the oral capsules.

Preferably, the capsules are designed to suitable sizes or compositions based on the age or physical characteristics of the patient as well as the severity of the disease. Such dosage forms are prepared using conventional methods known to those in the field of pharmaceutical formulation and described in the pertinent texts, (e.g., Remington: The Science and Practice of Pharmacy, Twentieth Ed. (Philadelphia, Pa.: Lippincott Williams & Wilkins, 2000)). Tablets and capsules represent the most convenient oral dosage forms, in which case solid pharmaceutical carriers are employed.

Tablets may be manufactured using standard tablet processing procedures and equipment. One method for forming tablets is by direct compression of a powdered, crystalline or granular composition containing the active agent(s), alone or in combination with one or more carriers, additives, or the like. As an alternative to direct compression, tablets can be prepared using wet-granulation or thy-granulation processes. Tablets may also be molded rather than compressed, starting with a moist or otherwise tractable material; however, compression and granulation techniques are preferred.

In those embodiments, wherein the dosage form is a capsule, the brain energy molecule-containing composition is typically encapsulated in the form of a solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. (See, for e.g., Remington: The Science and Practice of Pharmacy, supra), which describes materials and methods for preparing encapsulated pharmaceuticals.

Preferred solid dosage forms, whether tablets, capsules, caplets, or particulates, are preferably coated or have a coating so as to provide for delayed and sustained release. Dosage forms with delayed and sustained release coatings may be manufactured using standard coating procedures and equipment. (See, for e.g., Remington: The Science and Practice of Pharmacy, supra).

In a preferred embodiment, the oral tablet or capsules comprise a coating of a pH-dependent polymer. The pH-dependent polymer is preferably selected from the group consisting of: a polyacrylate material, a cellulose acetate phthalate, cellulose phthalate hydroxyl propyl methyl ether, polyvinyl acetate phthalate, hydroxyl propyl methyl cellulose acetate succinate, cellulose acetate trimellitate and shellac. In another preferred embodiment, the oral tablet further comprises a hydrophilic polymer. The hydrophilic polymer is preferably selected from the group consisting of: hydroxy propyl methylcellulose, hydroxypropyl ethylcellulose, hydroxypropyl cellulose, hydroxy ethylcellulose, methylcellulose, xantham gums, alginate salts, polyethylene oxide, carboxyvinyl polymer, and a salt of a carboxymethyl cellulose. The hydrophilic polymer preferably has a viscosity within the range of from about 60 to about 7,000,000 centipoises in a 2% by weight water solution at 25 degrees Celsius, as measured by a Brookfield LV viscometer. In another preferred embodiment, the oral tablet further comprises a water-insoluble polymer. The water-insoluble polymer is preferably selected from the group consisting of: ethyl cellulose, acetate cellulose and polyacrylate copolymer. The coatings provide for the delayed and the sustained release of the energy molecules.

One embodiment of the invention provides a method for treating nocturnal hypoglycemia. The method typically comprises administering the delayed and sustained release composition comprising the energy molecule to a subject in need thereof, immediately prior to going to sleep. In a preferred embodiment, the composition does not contain digestible substances thereby allowing the sleep cycle of the subject to not be disturbed while allowing subject to still receive the energy molecule required for human brain function. The method may also be useful for treating Alzheimer's disease and other CNS diseases.

Another embodiment of the invention provides a transdermal delivery device. The transdermal delivery device preferably comprises a reservoir layer, an adhesive layer, a backing layer and a release liner. The reservoir layer typically comprises absorbent materials inert to chemicals and preferably contains a composition comprising an energy molecule and a skin permeation enhancer formulation. In one embodiment, the reservoir layer is typically loaded up to saturation or super saturation with energy molecules to allow a high thermodynamic activity of the energy molecules.

In a preferred embodiment, the skin permeation enhancer formulation is the formulation described above. Other skin permeation enhancer formulations may also be used.

The adhesive layer is typically attached to the reservoir layer to secure and seal the device to the skin to prevent leaking. In order to allow the adhesive layer to secure and seal the device to the skin, the adhesive layer preferably has margins that extend farther than the reservoir layer to prevent leaking when the device is in use. Preferably, the backing layer is coated by the adhesive layer and, in a preferred embodiment, is impermeable to the energy molecule. In a preferred embodiment, the release liner is inert to chemicals and is configured to release the composition contained in the reservoir layer such that less than 10% (e.g., less than 5%) by weight of the energy molecule is released within 2 hours after administration, the energy molecule being released at a sustained rate after 2 hours for 8 hours or more.

The energy molecule used in the transdermal delivery device is the same as is found in the oral tablet. The energy molecule is typically one or more molecules selected from the group consisting of: glucose, mannose, lactic acid (lactate), and pyruvic acid (pyruvate).

The backing layer preferably comprises any material that is impermeable for the energy molecules and physically and chemically stable to the skin permeation enhancer formulation. In a preferred embodiment, the backing layer is comprised of a commercially available material, such as SCOTCHPAK by 3M, though other materials may be utilized. In other embodiments, the adhesive layer is coated to the backing and provides attachment for the reservoir and also surrounds and seals the reservoir onto the skin. The adhesive layer typically comprises any adhesive material that is physically and chemically compatible with the reservoir layer. In a preferred embodiment, the adhesive layer comprises EUDRAGIT acrylic adhesives. In another embodiment, the adhesive layer comprises NATIONAL STARCH acrylic adhesives. Other suitable adhesives may be used as well.

The reservoir layer typically comprises any absorbent material inert to the energy molecules and the skin permeation enhancer formulation. The absorbent material is fixed to the transdermal delivery device through adhesion to the adhesive layer on the backing layer. In a preferred embodiment, cotton fabric is utilized as the absorbent material. In another embodiment, polypropylene non-woven material is utilized as the absorbent material. Other absorbent materials may also be utilized in addition to these two options.

One embodiment of the invention provides a method for treating a subject having nocturnal hypoglycemia through use of the transdermal delivery device. In a preferred embodiment, the transdermal delivery device is placed anywhere on the subject's skin immediately prior to going to sleep. In a more preferred embodiment, the transdermal delivery device is placed anywhere on the subject's neck immediately prior to going to sleep. In a most preferred embodiment, the transdermal delivery device is placed on the subject's neck area proximate to the subject's carotid artery immediately prior to going to sleep.

In a preferred implementation of this method, the device is configured to load the composition into the reservoir layer after detaching the release liner and before applying the device to the skin. In such an embodiment, there may be a kit utilized which comprises a transdermal delivery device and a bottle of a composition comprising the energy molecule and skin permeation enhancer formulation. A subject detaches the release liner, fills the reservoir layer with the composition from the bottle, and then applies the device to the subject's neck proximate to the subject's carotid artery. In another implementation of this method, the reservoir layer is preloaded with the liquid mixture of energy molecules and enhancers.

Without being limited to any one mechanism, the methods of treating Alzheimer's disease and other CNS diseases involve maintaining a certain brain energy supply during sleep, which enables valuable dream activities during sleep that only can benefit general human health but also may prevent and reverse early stage of central nerve system degenerative diseases such as Alzheimer's disease and dementia. The methods comprising administering to the subject the delayed and sustained release composition of the invention, such as the oral tablet, capsule, or transdermal delivery composition.

Accordingly, in one aspect, the present invention is also directed to a system for brain stimulation during sleep. Though certain brain stimulation has been used to study the correlation between sleep stages and memory consolidation, the present invention is the first to disclose that providing brain stimulation to a sleeping subject may be used to enhance the vividness of dreams as well as direct the subject matter of the dreams. With increased vividness of dreams, the subject is more able to retain the content of dreams. In some implementations, the brain stimulation may be used to aid remembrance of past experiences. For example, the increased vividness of the related dream facilitates memorization of the dream contents so that the memory of the past experience may be recovered. Thus the system may be used for brain training. In some instances, system may inhibit memory loss due to dementia, for example Alzheimer's disease. The system may also inhibit mild cognitive impairment. The system comprises at least one of the following components: a brain energy supply source (which is the delayed and sustained release composition of the invention), a hypnotic, and a brain stimulation module. In preferred embodiments, the system comprises at the brain stimulation module.

In another aspect, the present invention is directed to methods of increasing vividness of a subject's dreams. The methods comprise administering to the subject, prior to the subject enters a period of sleep, a brain energy molecule and/or a hypnotic. The method may further comprise stimulating the subject with sensory stimulation when the subject is in restorative sleep.

In still another aspect, the present invention is directed to methods of directing the subject matter of a subject's dreams. The methods comprise administering to the subject a brain energy molecule in a delayed and sustained release formulation and stimulating the subject stimulating the subject with sensory stimulation when the subject is in restorative sleep. The methods may further comprise detecting brain activity of the subject and determining from the brain activity of the subject the subject is in restorative sleep. In some implementations, the methods comprise administering to the subject a hypnotic. The hypnotic may be in an immediate release formulation or a delayed and sustained release formulation. In some implementation, the brain activity of the subject is detected by recording the electrical activity of the subject's brain or by measuring movement of the subject's eyes.

For both methods of directing the subject matter of a subject's dreams and methods of increasing vividness of a subject's dreams, restorative sleep is Stage 3, Stage REM, or both. In preferred embodiment, the brain energy molecule is in a delayed and sustained release formulation. The hypnotic may also be in a delayed and sustained release formulation, or the hypnotic may be in a sustained release formulation. Preferably, a hypnotic with a short half-life (for example zolpidem) is in a formulation for delayed release and sustained release while a hypnotic with a long half-life (for example mirtazapine) is in a sustained release or immediate release formulation. The brain energy molecule and the hypnotic may be administered separately or together. In some embodiments, a second administration of the hypnotic may be needed while the subject is asleep.

The sensory stimulation may be sound, scent, taste, tactile, visual, or a combination thereof.

EXAMPLES

The following compositions, provided by way of example and not limitation, are related to a delayed and sustained release of energy molecules useful for brain function.

Example 1

An oral composition comprising 750 mg of glucose, 75 mg of hydroxyl ethyl cellulose and other conventional pharmaceutical ingredients, such as Magnesium Stearate as a lubricant. This composition is first granulated and then compressed into core tablets.

The core tablets are spray coated with polyacrylated copolymer aqueous solution (EUDRAGIT® NE 30 D). Finally, the tablets are coated with cellulose acetate phthalate (Aquacoat® CPD Cellulose Acetate Phthalate Aqueous Dispersion).

Example 2

A transdermal delivery device with a skin permeation enhancer formulation of:
76% Butylene Glycol, by weight,
6% monothioglycerol, by weight,
10% 2-methyl 3-Hydroxy Pyranones, by weight, and
8% Oleic Acid, by weight.

A suspension of enhancer mixture with a saturated energy molecule of Lactic acid was added to the Franz cell donor compartment, while the receiver compartment on the other side of skin contained PH 7.4 isotonic solution. The permeation test set was carried out at constant temperature of 32 degree C. for a period of 10 hours.

Example 3

Testing of a preferred embodiment for the oral formulations was carried out using USP dissolution method II. USP dissolution method II is well known in the art and is described in chapter 711 of Stage 6 Harmonization of The United States Pharmacopeia and The National Formulary, which is incorporated herein by reference. The preferred embodiment was tested using USP dissolution method II in a simulated gastric fluid dissolution media at 50 revolutions per minute for two hours, rinsed, and followed immediately after rinsing by testing in a simulated intestinal fluid dissolution media at 50 revolutions per minute for an extended period of time. Testing revealed that less than 5% of the energy molecule being released within 2 hours in the gastric fluid after administration, less than 60% of the energy molecule within the first 4 hours and at least 85% of the energy molecule being released within 8 hours after administration.

Example 4

Formulation 1. Zolpidem (6.25 mg) is mixed with glucose and the other ingredients before tableting for a delayed and sustained release formulation.

Example 5

Formulation 2. Formulation 1 is film-coated with a composition comprising zolpidem (6.25 mg) and ethylcellulose.

Example 6

Test Results

1. A healthy male adult volunteer was administered 2 caplets of delayed and sustained release glucose at bedtime. The subject reported that he had more vivid dreams with the administration of the delayed and sustained release glucose and was more able to recall past memory upon waking up.
2. A healthy male adult volunteer was treated using the system of the present invention. The subject was connected with brain simulation module and administered 3 caplets of delayed and sustained release glucose at bedtime prior to the subject going the sleep. The sensory stimulation received was sound stimulation during certain brain waves. The prerecorded sound play was a conversation between the subject's family members in a past event. Upon awakening, the subject reported that he could recall dreams related to the voice stimulation content, which expanded his memory of the past event.
3. A male adult volunteer was administered 2 caplets of delayed and sustained release of glucose with sustained release of zolpidem at bedtime. The subject reported that he experienced better sleep and found the dreams he had to be more vivid and memorable.
4. A 54-year-old healthy male subject, without diabetes, took 2 caplets of delayed and sustained release glucose at bedtime every day for one week. Subsequently, the subject 5 mg to 10 mg zolpidem in addition to the 2 caplets of delayed and sustained release glucose at bedtime every day for one week. The subject reported that he had more vivid dreams during both weeks. The subject also reported that he remembered more of the dreams in the mornings during both weeks, but the improvement was most noticeable when he took zolpidem. During the first week, the subject also checked his blood glucose levels at bedtime, between 2 to 3 am, and upon waking up in the morning. The average readings were 80 mg/L, 86 mg/L, and 85 mg/L.
5. A 58-year-old healthy male subject, without diabetes, took 2 caplets of delayed and sustained release of glucose at bedtime. The subject reported having more dreams while remembering more of dreams upon waking up.
6. A 62-year-old male diabetic subject was administered 2 caplets of delayed and sustained release glucose at bedtime every day for a week. For two of these days, the subject also took zolpidem at bedtime. The subject's diabetic treatment comprises taking Repaglinide, an insulin stimulator, 30 minutes before meals. While under this therapy, the subject reported a history of occasional nocturnal hypoglycemia. The subject reported that he had more dreams and remembered the dream when he woke up in the mornings. He found that the beneficial effect on dreams and memory was more pronounced when he also took zolpidem at bed time.
7. A 79-year-old male diabetic subject took 2-3 caplets of delayed and sustained release glucose at bedtime every day for a week. His diabetic treatment comprises taking short and medium acting insulin daily before meals. The subject said that he felt he has dreamt less since he started using the insulin product. After taking the delayed and sustained release glucose at bedtime, the subject reported that he had more dreams during night and recalled then after waking up.
8. A 63-year-old non-diabetic female with family history of Alzheimer's disease has been on Donepezil 5 mg daily for more than one year. MRI found abnormal shrinkage of her brain mass. After taking timed-release glucose tablets of the present invention (4AmGlucose™) at bedtime daily for three months, she reported that her normal memorable dreams have come back, which has been a very rare experience for years. She also reported that her memories of daily events and activities have been improved.

9. A 72-year-old non-diabetic male with family history of Alzheimer's disease has been on Donepezil 10 mg daily for two years. MRI found abnormal shrinkage of his brain mass. After taking timed-release of glucose tablets of the present invention (4AmGlucose™) daily at bedtime for two months, he reported that his frequent nightmares have disappeared and that his dreams are normal again. He felt that his daily memories are much improved too.

10. Three 120 to 160 lb healthy males (ages from 45 to 58) took one tablet of 1000 mg delayed and sustained release of glucose tablet at bedtime for up to 7 days. All three subjects experienced more vivid dreams towards wake up in the morning, elevated blood glucose levels around 2 am detected by taking fingertip blood samples or monitoring with continued glucose monitoring device (CGM).

11. A 62 years old female early stage Alzheimer's disease patient, 110 lb, took 1 tablet of 1000 mg delayed and sustained release of glucose at bedtime. Her frequent nightmares and night sweats were eliminated, and she started to have normal dream activities that she missed for many years.

12. An 83 years old male mid-stage Alzheimer's disease patient, 140 lb, took 1-2 tablets of 1000 mg delayed and sustained release of glucose at bedtime. His frequent nightmares and hallucinations after midnight were eliminated. He also woke up more energetic and feeling more normal.

13. An 85 year old female with type II diabetics on mid and long acting insulin products, took one delayed and sustained release tablet (1000 mg glucose) at bedtime. Her nocturnal hypoglycemia attack (symptoms includes seizure or coma) did not occurred.

Having herein set forth various embodiments of the present invention, it is anticipated that suitable modifications can be made thereto which will nonetheless remain within the scope of the invention. The invention shall therefore only be construed in accordance with the following claims below.

What is claimed is:

1. A delayed and sustained release transdermal preparation comprising:
   a brain energy molecule required for human brain function selected from the group consisting of: glucose, mannose, lactic acid, and pyruvic acid; and
   a skin permeation enhancer formulation, the skin permeation enhancer formulation comprising:
   10% to 95% by weight of at least one glycol selected from the group consisting of: propylene glycol, butylene glycol, hexylene glycol, ethoxydiglycol, dipropylene glycol, and pentylene glycol;
   1% to 10% by weight of monothioglycerol;
   2% to 30% by weight of at least one of 2-methyl-3-hydroxypyranone or 2-ethyl-3-hydroxypyranone, and
   2%-10% by weight of an aliphatic carboxylic acid of 8 to 24 carbon atoms or an ester of said acid with an aliphatic alcohol of 1 to 14 carbon atoms and 1 to 2 hydroxy groups,
   wherein less than 15% by weight of the brain energy molecule is released within 2 hours after administration, the brain energy molecule being released at a sustained rate after 2 hours, wherein less than 60% of the brain energy molecule is released within the first 4 hours and at least 80% of the brain energy molecule is released within 8 hours after administration.

2. A system for brain stimulation during sleep, the system comprising:
   a brain energy supply source, wherein the brain energy supply source is a delayed and sustained release tablet or transdermal preparation configured to release less than 15% by weight of a brain energy molecule within 2 hours after administration, after 2 hours the brain energy molecule is configured to release at a sustained rate with less than 60% of the brain energy molecule being released within the first 4 hours, and further configured to release at a sustained rate at least 80% of the brain energy molecule within 8 hours after administration,
   wherein:
   the brain energy molecule is selected from the group consisting of: glucose, mannose, lactic acid, and pyruvic acid,
   the delayed and sustained release tablet comprises:
      a core tablet comprising:
         250 mg to 1250 mg of the brain energy molecule; and
         a hydrophilic polymer;
      a water-insoluble polymer coating, wherein the water-insoluble polymer coating is applied to the core tablet; and
      a pH-dependent polymer coating, wherein the pH-dependent polymer coating is applied to the core tablet coated with the water-insoluble polymer coating, and
   the delayed and sustained release transdermal preparation comprises:
      the brain energy molecule; and
      a skin permeation enhancer formulation, the skin permeation enhancer formulation comprising:
         10% to 95%, by weight, at least one glycol selected from the group consisting of:
         propylene glycol, butylene glycol, hexylene glycol, ethoxydiglycol, dipropylene glycol, and pentylene glycol;
         1% to 10%, by weight, monothioglycerol;
         2% to 30%, by weight, at least one of 2-methyl-3-hydroxypyranone or 2-ethyl-3-hydroxypyranone, and
         2%-10%, by weight, an aliphatic carboxylic acid of 8 to 24 carbon atoms or an ester of said acid with an aliphatic alcohol of 1 to 14 carbon atoms and 1 to 2 hydroxy groups;
   a sensory stimulation unit;
   a recording unit, wherein the recording unit detects and records stages of sleep; and
   a program to interpret records from the recording unit and activate the sensory stimulation unit, wherein the program directs activation of the sensory stimulation unit upon detection by the recording unit of restorative sleep and the sensory stimulation unit delivers at least one sensory stimulation selected from the group consisting of: sound, scent, taste, tactile, and visual.

3. The system of claim 2, wherein the system further comprises a hypnotic source, a cholinergic molecule, or both.

4. The system of claim 2, wherein the recording unit detects brain waves and records electroencephalography or wherein the recording unit detects and records eye moments.

5. The system of claim 4, wherein the restorative sleep is Stage 3 sleep, Stage REM sleep, or both and wherein the program directs activation of the sensory stimulation unit upon the recording unit detecting the start of restorative sleep.

6. The system of claim 2, wherein the brain energy supply source is the transdermal preparation, the system further comprises a hypnotic source, a cholinergic molecule, both, wherein the hypnotic source and/or the cholinergic molecule is provided in a delayed and sustained release composition comprising:
   a core tablet comprising:
      a hypnotic, a cholinergic molecule, or both; and
      a hydrophilic polymer;
   a water-insoluble polymer coating, wherein the water-insoluble polymer coating is applied to the core tablet; and
   a pH-dependent polymer coating, wherein the pH-dependent polymer coating is applied to the core tablet coated with the water-insoluble polymer coating,
   wherein the delayed and sustained release composition is configured to release less than 60% of the hypnotic source, cholinergic molecule, or both within the first 4 hours after administration and to release at least 80% of the hypnotic source, cholinergic molecule or both within 8 hours after administration, wherein the hypnotic source, the cholinergic molecule, or both is released at a sustained rate 2 hours after administration.

7. The delayed and sustained release transdermal preparation of claim 1, wherein less than 10% by weight of the energy molecule is delivered to blood circulation within 2 hours after administration and the energy molecule is delivered at a sustained rate after 2 hours from administration for at least 8 hours after administration.

8. The delayed and sustained release transdermal preparation of claim 1, wherein the skin permeation enhancer formulation comprises:
   70-80%, by weight, butylene glycol,
   3-9%, by weight, monothioglycerol,
   10%, by weight, 2-methyl 3-hydroxy pyranone, and
   4-12%, by weight, oleic acid.

9. The delayed and sustained release transdermal preparation of claim 1, wherein the skin permeation enhancer formulation comprises:
   76%, by weight, butylene glycol,
   6%, by weight, monothioglycerol,
   10%, by weight, 2-methyl 3-hydroxy pyranone, and
   8%, by weight, oleic acid.

10. The delayed and sustained release transdermal preparation of claim 1 further comprising:
   a reservoir layer, wherein the reservoir layer contains the brain energy molecule required for human brain function and the skin permeation enhancer formulation and further comprises absorbent materials that are inert to the brain energy molecule and the skin permeation enhancer formulation;
   an adhesive layer, wherein the adhesive layer is attached to the reservoir layer whereby the adhesive layer seals the delayed and sustained release transdermal preparation to skin to prevent the reservoir layer from leaking;
   a backing layer, wherein the backing laying is adjacent to the adhesive layer and is impermeable to the brain energy molecule; and
   a release liner, wherein the release liner is inert to chemicals.

11. The delayed and sustained release transdermal preparation of claim 10, wherein the reservoir layer is loaded to saturation of the brain energy molecule.

12. The delayed and sustained release transdermal preparation of claim 10, wherein the reservoir layer comprises 250 mg to 1250 mg of the brain energy molecule.

13. The system of claim 2, wherein the brain energy supply source is the transdermal preparation, the transdermal preparation delivers less than 10% by weight of the energy molecule is delivered to blood circulation within 2 hours after administration and the energy molecule is delivered at a sustained rate after 2 hours from administration for at least 8 hours after administration.

14. The system of claim 2, wherein the brain energy supply source is the transdermal preparation.

15. The system of claim 2, wherein the brain energy supply source is the transdermal preparation, the skin permeation enhancer formulation comprises:
   70-80%, by weight, butylene glycol,
   3-9%, by weight, monothioglycerol,
   10%, by weight, 2-methyl 3-hydroxy pyranone, and
   4-12%, by weight, oleic acid.

16. The system of claim 2, wherein the brain energy supply source is the transdermal preparation, the skin permeation enhancer formulation comprises:
   76%, by weight, butylene glycol,
   6%, by weight, monothioglycerol,
   10%, by weight, 2-methyl 3-hydroxy pyranone, and
   8%, by weight, oleic acid.

17. The system of claim 2, wherein the brain energy supply source is the transdermal preparation, the system further comprises:
   a reservoir layer, wherein the reservoir layer contains the brain energy molecule required for human brain function and the skin permeation enhancer formulation and further comprises absorbent materials that are inert to the brain energy molecule and the skin permeation enhancer formulation;
   an adhesive layer, wherein the adhesive layer is attached to the reservoir layer whereby the adhesive layer seals the delayed and sustained release transdermal preparation to skin to prevent the reservoir layer from leaking;
   a backing layer, wherein the backing laying is adjacent to the adhesive layer and is impermeable to the brain energy molecule; and
   a release liner, wherein the release liner is inert to chemicals.

18. The system of claim 17, wherein the reservoir layer is loaded to saturation of the brain energy molecule.

19. The system of claim 3, wherein the core tablet further comprises the hypnotic source, the cholinergic molecule, or both.

* * * * *